United States Patent
Kim et al.

(10) Patent No.: US 11,013,580 B2
(45) Date of Patent: May 25, 2021

(54) METHOD OF MANUFACTURING A DENTAL CORD

(71) Applicant: AMOGREENTECH CO., LTD., Gimpo-si (KR)

(72) Inventors: Chan Kim, Gwangju (KR); Seung Hoon Lee, Paju-si (KR); Song Hee Koo, Seoul (KR); Ji Hyun Lee, Incheon (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 0 days.

(21) Appl. No.: 16/658,655

(22) Filed: Oct. 21, 2019

(65) Prior Publication Data
US 2020/0046472 A1 Feb. 13, 2020

Related U.S. Application Data

(62) Division of application No. 15/526,544, filed as application No. PCT/KR2015/013366 on Dec. 8, 2015, now abandoned.

(30) Foreign Application Priority Data

Dec. 17, 2014 (KR) .................... 10-2014-0182439

(51) Int. Cl.
*D01F 2/26* (2006.01)
*D01F 6/10* (2006.01)
(Continued)

(52) U.S. Cl.
CPC .......... *A61C 9/0033* (2013.01); *A61C 19/063* (2013.01); *A61L 31/048* (2013.01);
(Continued)

(58) Field of Classification Search
CPC .......... A61C 9/0033; B29C 2793/0063; B32B 37/153; B32B 38/0004; B32B 2038/0045;
(Continued)

(56) References Cited

U.S. PATENT DOCUMENTS

| 4,321,038 A | 3/1982 | Porteous |
| 4,522,593 A | 6/1985 | Fischer |

(Continued)

FOREIGN PATENT DOCUMENTS

| KR | 100575471 | 5/2006 |
| KR | 20090040188 | 4/2009 |

(Continued)

OTHER PUBLICATIONS

Translation of KR 20110047340 A (published on May 9, 2011).*
International Search Report—PCT/KR2015/013366 dated Mar. 7, 2016.

*Primary Examiner* — Leo B Tentoni
(74) *Attorney, Agent, or Firm* — Cantor Colburn LLP

(57) ABSTRACT

Provided is a method of manufacturing a dental cord. The method including: producing a spinning solution by dissolving a fiber-moldable hydrophobic polymer material in a solvent; spinning the spinning solution to obtain a polymer nanofiber web composed of nanofibers and including three-dimensional micropores; laminating the polymer nanofiber web to obtain a polymer membrane; slitting the polymer membrane to obtain a nanofiber tape yarn; hydrophilic-treating the nanofiber tape yarn to obtain a hydrophilic-treated nanofiber tape yarn; plying and twisting the hydrophilic-treated nanofiber tape yarn with a covered yarn to obtain a nanofiber multiple yarn; and impregnating the nanofiber multiple yarn with a hemostatic agent.

6 Claims, 8 Drawing Sheets

(51) Int. Cl.

| | | |
|---|---|---|
| D01F 6/12 | (2006.01) | |
| D01F 6/14 | (2006.01) | |
| D01F 6/16 | (2006.01) | |
| D01F 6/22 | (2006.01) | |
| D01F 6/60 | (2006.01) | |
| D01F 6/70 | (2006.01) | |
| D02G 1/02 | (2006.01) | |
| D02G 3/04 | (2006.01) | |
| D02G 3/06 | (2006.01) | |
| D02G 3/38 | (2006.01) | |
| D02J 1/22 | (2006.01) | |
| D04H 3/16 | (2006.01) | |
| A61C 9/00 | (2006.01) | |
| A61L 31/16 | (2006.01) | |
| D02G 3/36 | (2006.01) | |
| A61C 19/06 | (2006.01) | |
| A61L 31/04 | (2006.01) | |
| A61L 31/14 | (2006.01) | |
| D01D 4/02 | (2006.01) | |
| D01D 5/00 | (2006.01) | |
| D01D 7/00 | (2006.01) | |
| D01F 8/04 | (2006.01) | |
| D02G 3/40 | (2006.01) | |
| D02G 3/44 | (2006.01) | |
| D01F 6/18 | (2006.01) | |
| D01D 5/42 | (2006.01) | |
| B32B 38/00 | (2006.01) | |
| B32B 37/15 | (2006.01) | |

(52) U.S. Cl.
CPC ............ *A61L 31/146* (2013.01); *A61L 31/16*
(2013.01); *D01D 4/02* (2013.01); *D01D*
*5/0061* (2013.01); *D01D 7/00* (2013.01);
*D01F 8/04* (2013.01); *D02G 3/36* (2013.01);
*D02G 3/40* (2013.01); *D02G 3/448* (2013.01);
*A61L 2300/418* (2013.01); *A61L 2400/12*
(2013.01); *B29C 2793/0063* (2013.01); *B32B*
*37/153* (2013.01); *B32B 38/0004* (2013.01);
*D01D 5/0038* (2013.01); *D01D 5/426*
(2013.01); *D01F 6/18* (2013.01); *D10B*
*2201/26* (2013.01); *D10B 2321/041* (2013.01);
*D10B 2321/042* (2013.01); *D10B 2321/06*
(2013.01); *D10B 2321/08* (2013.01); *D10B*
*2321/10* (2013.01); *D10B 2321/121* (2013.01);
*D10B 2331/02* (2013.01); *D10B 2331/10*
(2013.01); *D10B 2509/00* (2013.01)

(58) Field of Classification Search
CPC ........ D01D 5/003; D01D 5/0038; D01D 5/04;
D01D 5/06; D01D 5/12; D01D 5/42;
D01D 5/426; D01D 7/00; D01F 2/26;
D01F 6/10; D01F 6/12; D01F 6/14; D01F
6/16; D01F 6/18; D01F 6/22; D01F 6/60;
D01F 6/70; D02G 1/02; D02G 3/04;
D02G 3/06; D02G 3/36; D02G 3/38;
D01J 1/22; D04H 3/16; D10B 2201/26;
D10B 2321/041; D10B 2321/042; D10B
2321/06; D10B 2321/08; D10B 2321/10;
D10B 2321/121; D10B 2331/02; D10B
2331/10
USPC ....... 264/103, 147, 160, 182, 184, 185, 187,
264/205, 206, 207, 208, 210.3, 210.8,
264/211.12, 211.14, 211.15, 331.11,
264/331.14, 331.18, 331.19, 331.21, 464,
264/465, 466, 484; 156/167, 181, 229,
156/244.11, 244.17, 244.19, 271; 57/3,
57/31, 210, 236, 238, 260, 314
See application file for complete search history.

(56) References Cited

U.S. PATENT DOCUMENTS

| | | | |
|---|---|---|---|
| 4,892,482 | A | 1/1990 | Lococo |
| 7,168,951 | B2 | 1/2007 | Fischer et al. |
| 2002/0081550 | A1 | 6/2002 | Karazivan et al. |
| 2006/0094320 | A1 | 5/2006 | Chen et al. |
| 2008/0003538 | A1* | 1/2008 | Wittrock ............... A61C 9/0033 433/136 |
| 2008/0096164 | A1 | 4/2008 | Fischer |
| 2008/0170982 | A1 | 7/2008 | Zhang et al. |
| 2011/0076197 | A1* | 3/2011 | Kook .................. D01D 5/0007 156/244.11 X |
| 2011/0229849 | A1 | 9/2011 | Maurer et al. |
| 2013/0115837 | A1 | 5/2013 | Kitchen et al. |
| 2014/0087330 | A1 | 3/2014 | Discko et al. |
| 2015/0152852 | A1 | 6/2015 | Li et al. |
| 2016/0157978 | A1 | 6/2016 | Tutak |

FOREIGN PATENT DOCUMENTS

| | | |
|---|---|---|
| KR | 20110047340 | 5/2011 |
| KR | 101075882 | 10/2011 |
| KR | 20130010058 | 1/2013 |
| KR | 101237436 | 3/2013 |
| WO | 2008051644 | 5/2008 |

\* cited by examiner

METHOD OF MANUFACTURING A DENTAL CORD

This application is a divisional application of U.S. application Ser. No. 15/526,544 filed May 12, 2017, which is a national entry of International Application No. PCT/KR2015/013366, filed on Dec. 8, 2015, which claims a priority to and the benefit of Korean Patent Application No. 10-2014-0182439, filed on Dec. 17, 2014, the contents of which in their entirety are herein incorporated by reference.

TECHNICAL FIELD

The present invention relates to a dental cord and a method of manufacturing the same, and more particularly, to a dental cord using nanofiber multiple yarns and a method of manufacturing the same.

BACKGROUND ART

Gingival retraction is a technique that accurately models the shape of the teeth hidden in the gingiva when modeling a gold or porcelain impression, in dental clinics in which a gingival retraction cord of slender yarns is inserted between the teeth and the gums, that is, in the gingival sulcus, to temporarily retract the gums from the teeth, without causing damages on the gums.

Gingival retraction cords (dental cords) are made of textile materials such as wools, cottons, or silks, and are classified into twisted cords, braided cords and knitted cords depending on the shape and degree of kinking.

These dental cords (gingival retraction cords) exhibit some differences depending on products, and are represented by ultrathin (#0), thin (#1), medium (#2), and thick (#3) according to thickness. Using hemostasis and gingival contraction (convergence) effect of the gingival sulcus, the dental cords perform the hemostasis of the blood remaining in the gingival sulcus in the mouth, reduce moisture such as saliva, tissue fluid, etc., and physically expose the marginal margin of the cervix through opening of the gingival sulcus. In addition, the dental cords can be used to obtain an impression for making dental prosthesis, for filling of direct cervical restoration (amalgam, composite resin, GI (Glass lonomer) restoration and cement, temporary filler), and for making indirect restoration (inlays, onlays, and all-optical tubes), and are used as an indispensable tool to prevent the bleeding of the gingival sulcus for securing the view of the operator and implantation of the abutment of the implant and the preparation of the final prosthesis of the implant.

Korean Patent Application Publication No. 10-2013-0010058 (Patent Document 1) discloses a method of manufacturing a cord for shrinking gums using cotton yarns, and a method of using a conventional dental cord dressed with a hemostatic agent (astringent agent).

However, in the case of the conventional dental cord disclosed in Patent Document 1, the use of natural fibers such as cotton, silk, and wool may cause the gingival sulcus to be excessively opened or permanently opened by the thickness of the fibers of tens to hundreds of micrometers (μm), and may tend to cause the excessive use of the drug of hemostatic agent, etc.

In addition, as shown in FIG. 1, since a filament is made in the form of spun yarns in order to make short fibers into long fibers, there were a disadvantage that a large amount of lint is generated, and a disadvantage that the filament should be made into a knitted type yarn by using special equipment in order to impart elasticity.

DISCLOSURE

Technical Problem

The present invention has been made to solve the above-mentioned problems, and its object is to provide a dental cord using a nanofiber multiple yarn having a large specific surface area and a large number of three-dimensional pores, thereby effectively impregnating a drug such as a hemostatic agent, and a method of manufacturing the dental cord.

Another object of the present invention is to provide a dental cord in which the tensile strength, elasticity, and thickness of a fiber can be easily adjusted by twisting only a nanofiber tape yarn alone or multiplying a nanofiber tape yarn and a natural fiber, to effectively manufacture a 2-ply twisted yarn and a 3-ply twisted yarn, and a method of manufacturing the dental cord.

Still another object of the present invention is to provide a dental cord using a nanofiber multiple yarn which is capable of achieving sufficient elasticity and water absorption even when the dental cord is not made into a knitted type yarn form by combining many pores and nanofiber multiple yarns of nanofiber tape yarns with hydrophilic natural fibers, and a method of manufacturing the dental cord.

Yet another object of the present invention is to provide a dental cord using a nanofiber multiple yarn having a simple manufacturing process and a method of manufacturing the dental cord.

Technical Solution

In order to achieve the above object, according to an aspect of the present invention, there is provided a dental cord comprising: a nanofiber multiple yarn which is obtained by plying and twisting at least two nanofiber tape yarns and which is impregnated with a drug, wherein the at least two nanofiber tape yarns are integrated by nanofibers made of fiber moldability polymer materials and having an average diameter of less than 1 μm, to thus be formed of a nanofiber web having three-dimensional micropores.

Preferably but not necessarily, the nanofiber multiple yarn may be formed by plying and twisting two or three nanofiber tape yarns.

Preferably but not necessarily, in addition, the nanofiber multiple yarn may be configured so that a covered yarn (or a core yarn) is covered with the nanofiber tape yarn. Preferably but not necessarily, in this case, the covered yarn may be made of natural fibers so as to impregnate a lot of drugs such as hemostatic agents.

Preferably but not necessarily, the nanofiber tape yarn may be obtained by slitting the nanofiber web at a width of 0.1 mm to 10 mm.

Preferably but not necessarily, the basis weight of the nanofibers is set in the range of 0.5 gsm to 50 gsm (gram per square meter) based on the entire spinning solution, the average pore size of the nanofiber web is set to 0.2 μm to 1.0 μm, and the fiber diameter is set to 0.05 μm to 1 μm.

According to another aspect of the present invention, there is provided a method of manufacturing a dental cord, the method comprising the steps of: producing a spinning solution, by dissolving a fiber-moldability polymer material in a solvent to prepare a spinning solution; spinning the spinning solution to obtain a polymer nanofiber web composed of nanofibers having an average diameter of less than 1 μm; laminating the nanofiber web to obtain a polymer membrane; slitting the polymer membrane to obtain a nanofiber tape yarn; plying and twisting the nanofiber tape yarn to obtain a nanofiber multiple yarn; and impregnating the nanofiber multiple yarn with a hemostatic agent.

Preferably but not necessarily, the nanofiber multiple yarn may be configured so that a covered yarn made of natural fibers is covered with the nanofiber tape yarn, the nanofiber tape yarn may be a hydrophilic polymer or a hydrophobic polymer, and may be processed to be hydrophilic.

Preferably but not necessarily, the method of manufacturing the dental cord may further comprise the step of thermally stretching the nanofiber multiple yarn obtained by plying and twisting the yarn between a glass transition temperature (Tg) and a melting temperature (Tm) of the polymer.

Advantageous Effects

As described above, the dental cord using the nanofiber multiple yarn according to the present invention has a relatively small diameter of the fiber compared to that of a conventional material, and thus has a large specific surface area and a large number of three-dimensional pores, to accordingly effectively impregnate a drug such as a hemostatic agent by using the nanofiber multiple yarn. As a result, applying such a dental cord effectively achieves a hemostatic and gingival contraction (convergence) effect when the gingiva is opened.

In addition, according to the present invention, the tensile strength, elasticity, and thickness of a fiber can be easily adjusted even when the dental cord is not made into a knitted type yarn form by twisting only a nanofiber tape yarn alone or multiplying a nanofiber tape yarn and a natural fiber, to effectively manufacture a 2-ply twisted yarn and a 3-ply twisted yarn.

In addition, according to the present invention, since a nanofiber tape yarn having many pores is combined with hydrophilic natural fibers, sufficient elasticity and moisture absorption can be achieved even when the dental cord is not made into a knitted type yarn form.

Further, according to the present invention, it is possible to manufacture a cord capable of eliminating a process of making a knitted type yarn by using special equipment and giving elasticity by a simple twisting process, thereby simplifying a manufacturing process.

In addition, according to the present invention, it is possible to manufacture a multiple yarn by twisting a nanofiber tape yarn obtained by slitting nanofiber after spinning the nanofibers, by using a conventional twister, so that existing manufacturing equipment can be used as it is, to thus further improve handle-ability, mass productivity and uniformity as well as save a manufacturing cost.

BRIEF DESCRIPTION OF DRAWINGS

FIGS. 5C and 5D schematically illustrate a method of manufacturing a nanofiber multiple yarn by using a nanofiber tape yarn according to second and third preferred embodiments of the present invention, in which FIG. 5C shows a nanofiber multiple yarn prepared by single-covering a covered yarn with a nanofiber tape yarn, and FIG. 5D shows a nanofiber multiple yarn prepared by double-covering a covered yarn with an intermediate yarn and a nanofiber tape yarn.

BEST MODE

Figure 1:
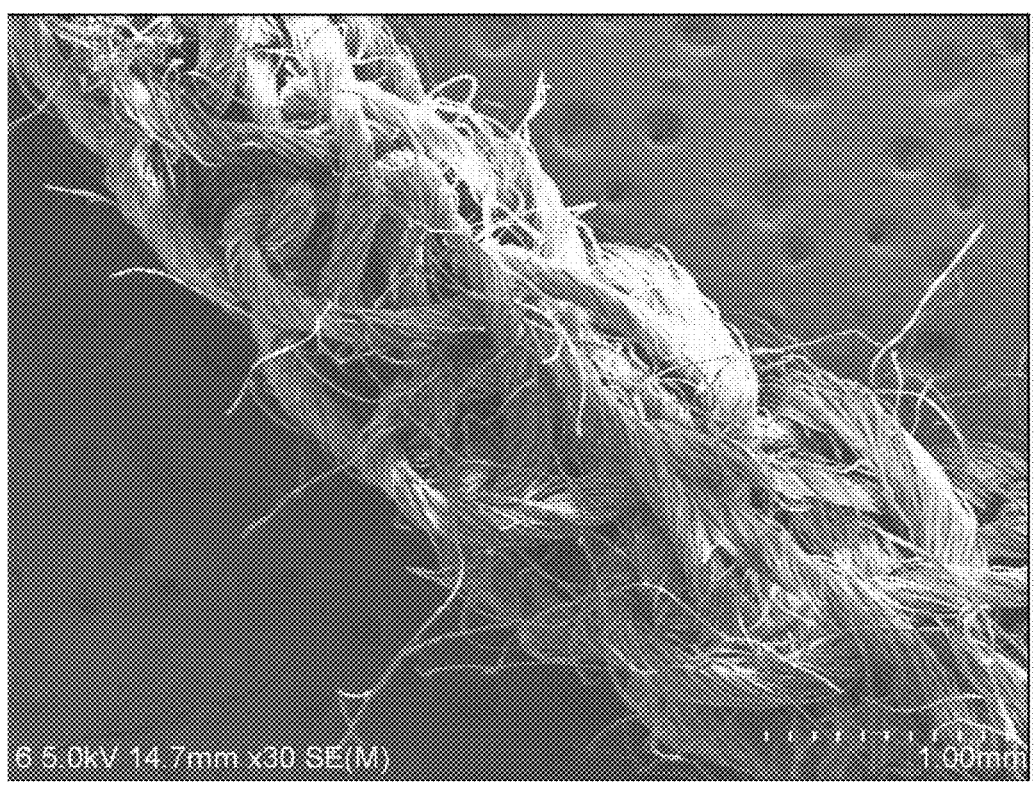
FIG. 1 is a scanning electron microscope (SEM) image showing a conventional commercialized retraction cord or dental cord made in the form of a knitted type yarn in order to spin short fibers to then be made into long fibers and impart elasticity.

The above and other objects, features and advantages of the present invention will become more apparent from the following description taken in conjunction with the accompanying drawings, and it will be apparent to those skilled in the art that the technical idea of the invention can be easily implemented and various modifications and variations can be made in the present invention without departing from the spirit or scope of the invention.

In the following description, detailed description of known functions or constructions relevant to the invention will be omitted since they would obscure the invention unnecessarily.

As shown in FIGS. 5A to 5D, a nanofiber multiple yarn according to first to third embodiments that are respectively used in a dental cord of the present invention is configured in any one structure of a nanofiber multiple yarn 10 made of only nanofibers obtained by plying and twisting nanofiber tape yarns 11 and 13, a nanofiber multiple yarn 10a made by single-covering a covered yarn 21 with a nanofiber tape yarn 11, and a nanofiber multiple yarn 10b made by double-covering a covered yarn 21 with an intermediate yarn 23 and a nanofiber tape yarn 11.

First, referring to FIGS. 2A, 3, 4A, and 4B, as well as FIGS. 5A to 5D, a nanofiber multiple yarn 10 having nanofibers is prepared by a manufacturing process including the steps of: preparing a spinning solution by dissolving a fiber moldability polymer material in a solvent (S11); producing a polymer nanofiber web 3 by spinning the spinning solution to thus spin nanofibers 1 of an average diameter less than 1 μm and then capture the spun nanofibers 1 (S12);

producing a polymer membrane 5 by laminating the polymer nanofiber web 3 (S13); producing nanofiber tape yarns 11 and 13 by slitting the polymer membrane 5 (S14); and producing the nanofiber multiple yarn 10 by plying and twisting the nanofiber tape yarns 11 and 13 (S15).

Figure 2A:
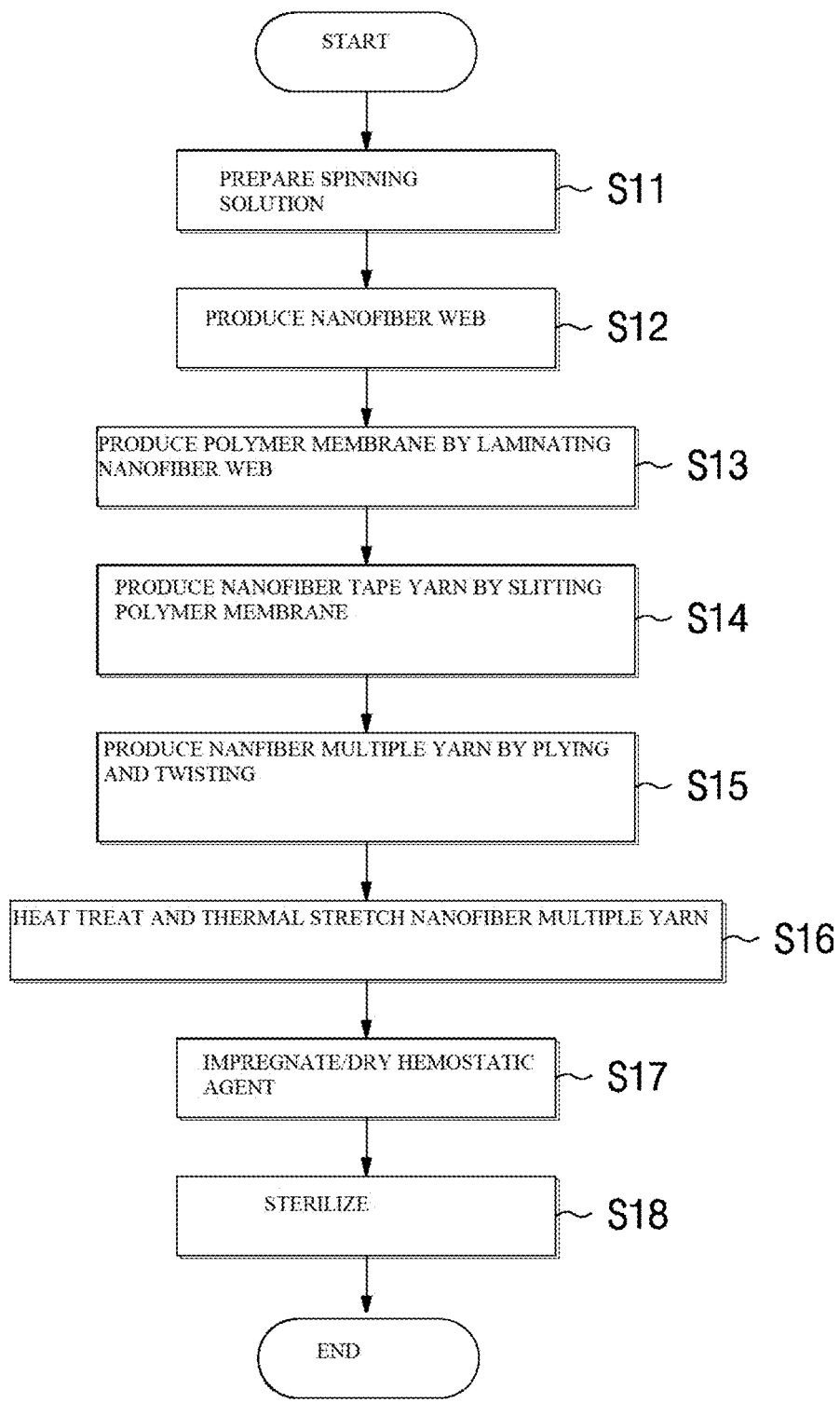
FIGS. 2A and 2B are manufacturing process flowcharts respectively illustrating a method of manufacturing a dental cord by using a nanofiber multiple yarn according to a preferred embodiment of the present invention.
Figure 2B:
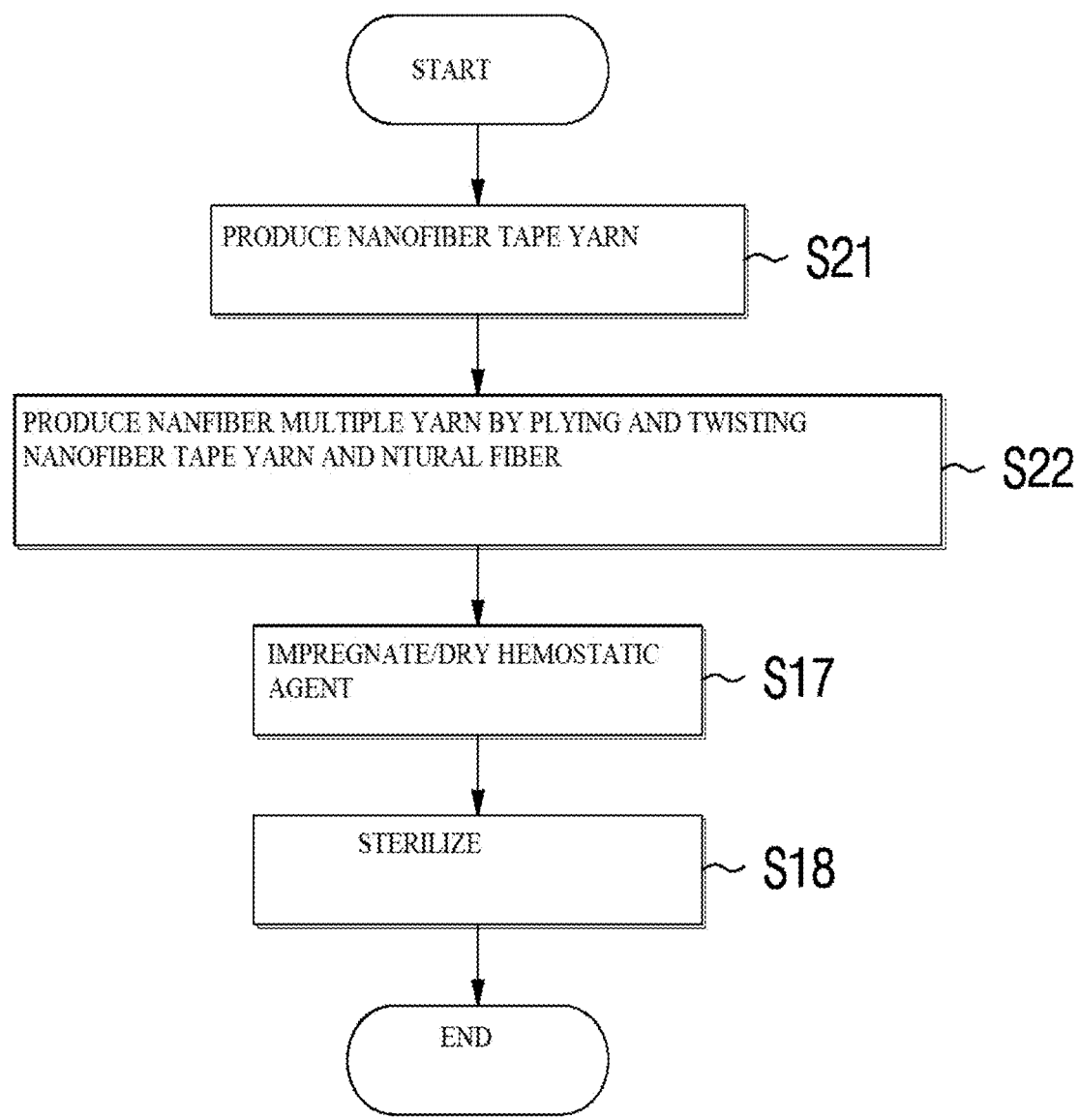
Figure 5A:
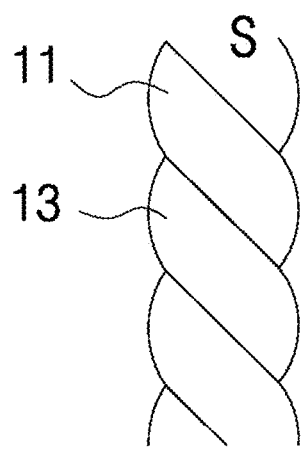
FIG. 5A is a schematic view showing a right-handed twisted yarn (S-twisted yarn) of a nanofiber multiple yarn composed of only nanofibers obtained by plying and twisting a nanofiber tape yarn according to a first preferred embodiment of the present invention.
Figure 5B:
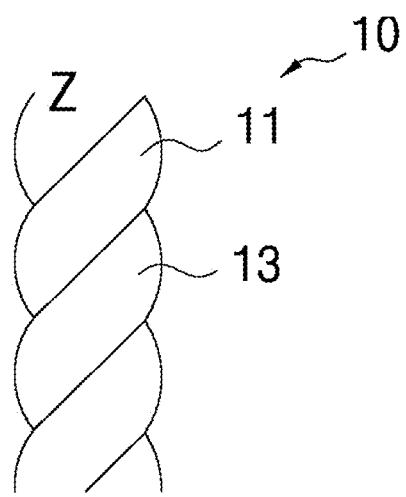
FIG. 5B is a schematic view showing a left-handed twisted yarn (Z-twisted yarn) of a nanofiber multiple yarn composed of only nanofibers obtained by plying and twisting a nanofiber tape yarn according to the first preferred embodiment of the present invention.
Figure 5C:
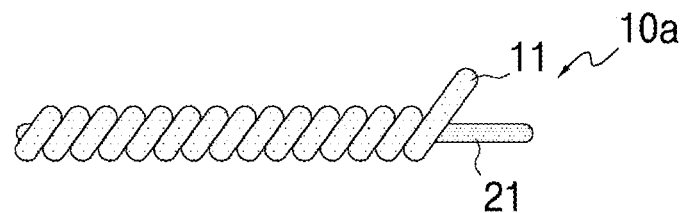
Figure 5D:
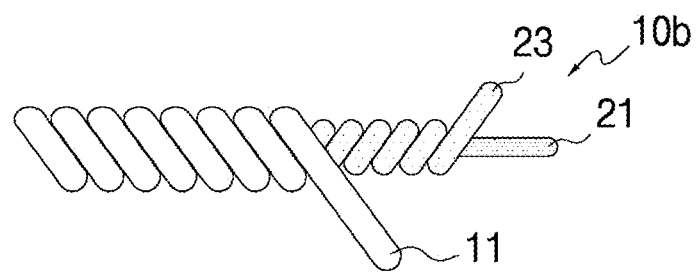

In addition, as shown in FIGS. 2B, 5C and 5D, the nanofiber tape yarn 11 can be plied and twisted together with the covered yarn 21 to obtain a nanofiber-containing multiple yarn 10a, or the nanofiber tape yarn 11 and the intermediate yarn 23 can be plied and twisted together with the covered yarn 21 to obtain a nanofiber-containing multiple yarn 10b (S22).

Hereinafter, a method of producing a nanofiber multiple yarn containing nanofibers according to the present invention will be described in detail by step-specific with reference to the drawings.

(Spinning Solution Preparing Step) (S11)

First, a fiber moldability polymer material is dissolved in an appropriate solvent to prepare a spinning solution having a spinnable concentration.

The content of the polymer material in the preparation of the spinning solution is suitably about 5 wt % to 50 wt %. When the content of the polymer material is less than 5 wt %, the nanofibers are not formed but are sprayed in a bead form, and thus it is difficult to form a membrane. Meanwhile, when the content of the polymer material exceeds 5 wt %, the viscosity of the spinning solution is too high, and thus the spin-ability is poor to cause it difficult to form fibers. Therefore, although there is no particular restriction on the preparation of the spinning solution, it is preferable to control the morphology of the fiber at a concentration that is easy to form a fibrous structure.

Examples of the polymer usable in the present invention may be configured by using one or multiplying two or more selected from the group consisting of polyvinylidene fluoride (PVdF), nylon, nitrocellulose, polyurethane (PU), polycarbonate (PC), polystryene (PS), polyacrylonitrile (PAN), polylatic acid (PLA), polylactic-co-glycolic acid (PLGA), polyethyleneimine (PEI), polypropyleneimine (PPI), polymethylmethacrylate (PMMA), polyvinylcholide (PVC), polyvinylacetate (PVAc), polystyrene divinylbenzene copolymer, polyvinyl alcohol (PVA), polyvinyl acetate (PVAc), and polyvinyl pyrrolidone (PVP). Any fiber moldability polymers that can be manufactured in a fibrous form by electrospinning include thermoplastic or thermosetting polymers. Therefore, the polymer usable in the present invention is not particularly limited to the above-mentioned polymer material.

In this case, hydrophilic polymers such as polyvinyl alcohol (PVA) and polyvinyl acetate (PVAc) may be preferably possible to impregnate a large amount of a hemostatic agent very easily into the pores in a subsequent process of impregnating the hemostatic agent.

In addition, the solvent which can be used in the present invention may employ one or a mixture of two or more selected from the group consisting of dimethylformamide (DMF), dimethylacetamide (DMAc), tetrahydrofuran (THF), acetone, alcohols, chloroform, dimethyl sulfoxide (DMSO), dichloromethane, acetic acid, formic acid, N-methylpyrrolidone (NMP), fluoric alcohols, and water.

(Nanofiber Web Producing Step) (S12)

Figure 3:
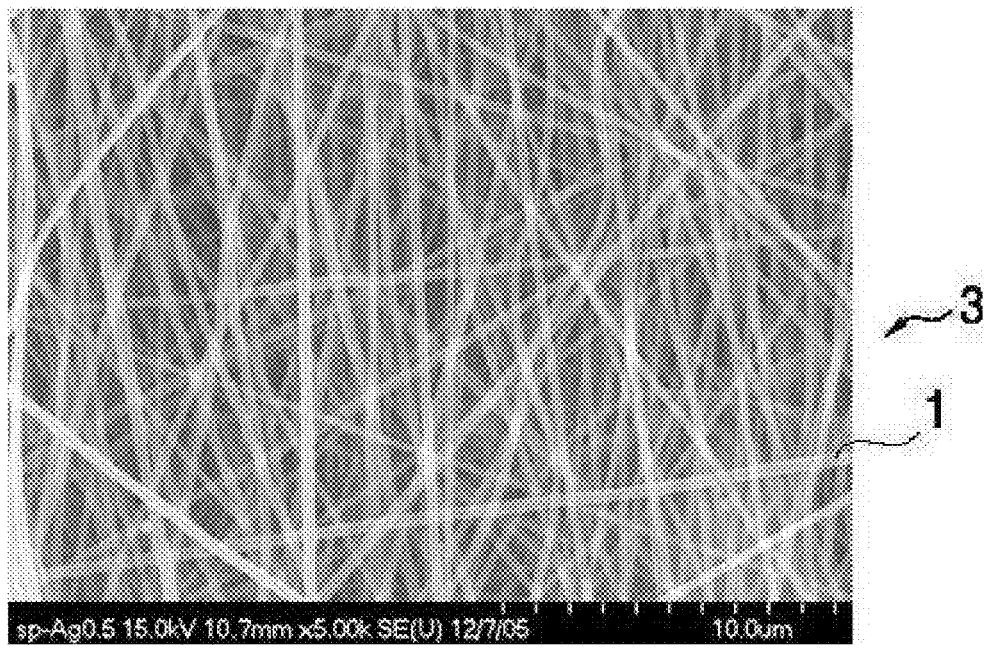
FIG. 3 is a scanning electron microscope (SEM) image of a nanofiber web (membrane) prepared in accordance with an embodiment of the present invention.

The prepared spinning solution is transferred to a spin pack by using a metering pump of an electrospinning device and a high voltage is applied to a nozzle of the spinning pack by using a high voltage regulator to spin nanofibers 1 having an average diameter of less than 1 μm, and then collect the spun nanofibers 1 to be a basis weight of 0.5 gsm to 100 gsm (gram per square meter), thereby produce a polymer nanofiber web (see FIG. 3).

In this case, the voltage to be used can be adjusted from 0.5 kV to 100 kV, and a collector plate can be grounded or charged with negative (−) polarity. Here, it is preferable that the collector plate should be made of an electroconductive metal or peeling paper. In the case of the collector plate, it is advisable to use a suction collector in order to smooth focusing of fibers during spinning.

It is also preferable to adjust the distance between the spin pack and the collector plate to 5 cm to 50 cm. It is preferable that a discharge amount during spinning should be discharged and spun by using a metering pump, and the spinning is performed in an environment of a relative humidity of 30% to 80% in a chamber capable of controlling temperature and humidity during spinning.

Meanwhile, examples of spinning methods that can be used in the present invention include electrospinning, electrospray, electroblown spinning, centrifugal electrospinning, and flash electrospinning.

Here, the basis weight is defined as the amount of spinning per unit area of the polymer.

When the basis weight of the polymer used is less than 0.5 gsm, the handling property is lowered and the slitting process tends to be unstable. When the basis weight of the polymer used is more than 100 gsm, the subsequent laminating process is not smoothly performed, and the process cost increases. In addition, the thickness of the final multiple yarn can be controlled through processes such as plying of yarns, twisting of yarn, and thermal stretching.

In addition, the average pore size of the produced nanofiber web is preferably in the range of 0.2 μm to 1.0 μm.

(Polymer Membrane Producing Step of Laminating Nanofiber Web) (S13)

Figure 4A:
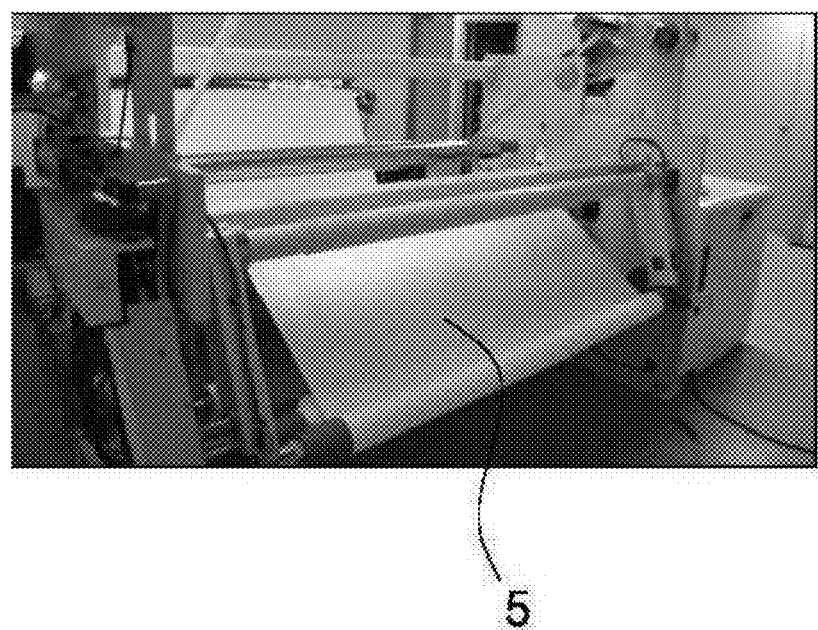
FIG. 4A is a photograph illustrating a process of laminating a nanofiber web according to the present invention.

The produced nanofiber web 3 is laminated by one of the methods of compression, calendering, rolling, thermal bonding, ultrasonic bonding and seam sealing tape to produce a polymer membrane 5 having a basis weight of 0.5 gsm to 100 gsm (see FIG. 4A). In some embodiments of the present invention, laminating is a step of forming a nanofiber web into a film by pressing and fixing the respective spun fibers by a method of a heat treatment, an ultrasonic wave or the like so as to prevent the fibers from moving.

In addition, lamination can be carried out with heat treatment, and preferably carried out at a temperature in the range of 20° C. to 250° C. in which the polymer used is not melted. If the temperature is less than 20° C., the fusion between the nanofibers is unstable due to too a low heat treatment temperature, or if the polymer having a high glass transition temperature is hardly fused between the nanofibers, there is a high possibility that the subsequent slitting does not proceed smoothly at the time of producing a tape yarn. Also, when the heat treatment temperature exceeds 250° C., it is undesirable that there is a high possibility that the polymer constituting the nanofiber is melted and thus the fibrous structure is lost.

(Nanofiber Tape Producing Step) (S14)

Figure 4B:
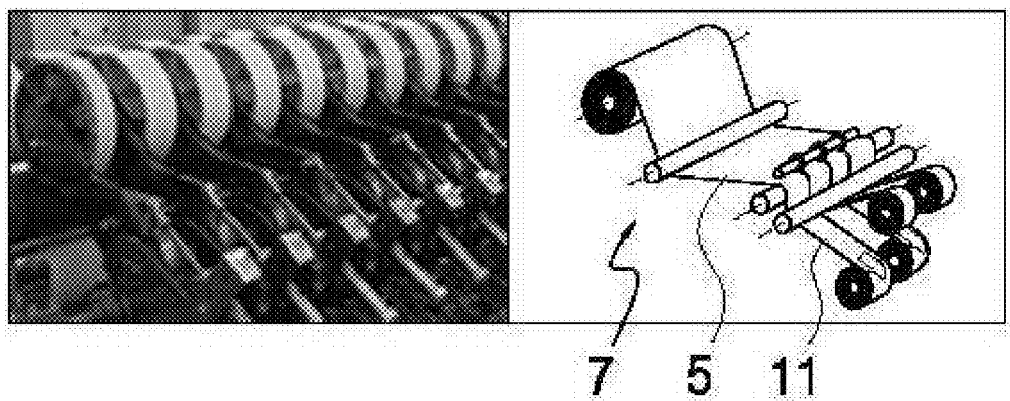
FIG. 4B is a schematic diagram illustrating a process of producing a nanofiber tape yarn by slitting a polymer membrane according to the present invention.

The laminated polymer membrane 5 is slitted to have a width of 0.1 mm to 10 mm by using various methods such as a cutter or a slitter 7 to produce nanofiber tape yarns 11 and 13 made of nanofibers (see FIG. 4B).

When the nanofiber tape yarns 11 and 13 are slitted at a the width of less than 0.1 mm, the width is too small to smoothly cut using the slitter, and the probability of occurrence of yarn breakage in tension and twisting is increased. Further, when the nanofiber tape yarns 11 and 13 are slitted at the width in excess of 10 mm, there is a disadvantage that the twist becomes large and unevenly occurs in the twisting step, and the final multiple yarn becomes thick. Therefore, the nanofiber tape yarns 11 and 13 preferably have a basis weight of 0.5 gsm to 100 gsm and a width of 0.1 mm to 10 mm.

(Nanofiber Multiple Yarn Producing Step) (S15)

Then, plying and twisting are carried out using the nanofiber tape yarn 11.

According to the plying and twisting steps, in the case of producing the nanofiber multiple yarn 10 composed of only nanofibers by plying and twisting the nanofiber tape yarns 11 and 13, the nanofiber tape yarn 11 and the nanofiber tape yarn 13 are plied in the plying step, respectively, and thereafter, are continuously subjected to the twisting step in the manner of a right-handed twisted yarn (S-twisted yarn) or a left-handed twisted yarn (Z-twisted yarn) as shown in FIGS. 5A and 5B, to thereby produce the nanofiber multiple yarn 10. Here, the nanofiber tape yarns 11 and 13 may be fabricated by using the same kind of polymer, and may also be made up by plying different types of nanofiber tape yarns.

Figure 6A:
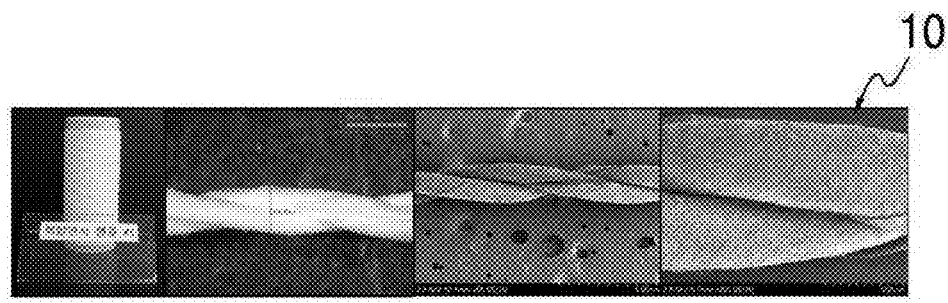
FIGS. 6A and 6B are a scanning electron microscope (SEM) image of the nanofiber multiple yarn prepared according to the first preferred embodiment of the present invention.
Figure 6B:
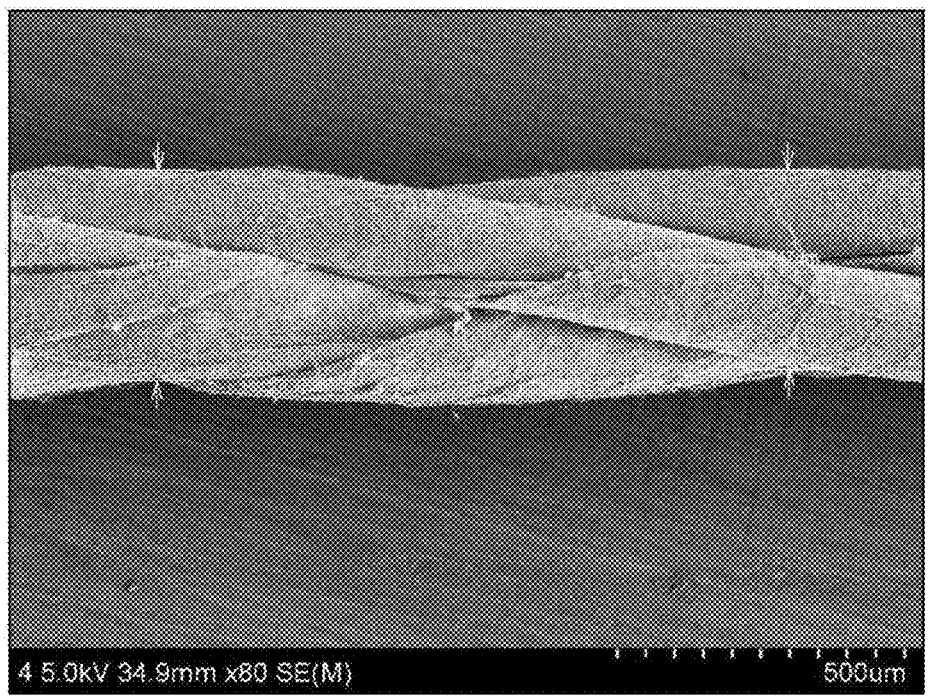

In this case, when the two nanofiber tape yarns 11 and 13 are twisted, the 2-ply twisted yarn is obtained as shown in FIG. 6A. When the three nanofiber tape yarns 11 and 13 are plied and then twisted, the 3-ply twisted yarn is obtained as shown in FIG. 6B.

In addition, in the case of producing the nanofiber multiple yarn 10a formed by single-covering the covered yarn 21 with the nanofiber tape yarn 11 as shown in FIG. 5C, or the nanofiber multiple yarn 10b formed by double-covering the covered yarn 21 with the nanofiber tape yarn 11 and the intermediate yarn 23 as shown in FIG. 5D, it is preferable that the nanofiber tape yarn 11 should be prepared as described above (S21) and then the non-tensioned covered yarn 21 and the tensioned nanofiber tape yarn 11 are plied and twisted so that the covered yarn 21 does not protrude outward (S22), as shown in FIG. 2B.

The nanofiber multiple yarn 10a shown in FIG. 5C is the 2-ply twisted yarn and the nanofiber multiple yarn 10b shown in FIG. 5D is the 3-ply twisted yarn.

The covered yarn 21 or the intermediate yarn 23 can employ various kinds of yarns by using natural fibers such as cotton yarn, silk yarn and paper yarn in accordance with their use, and are not particularly limited thereto.

In this case, in the case of producing the nanofiber tape yarn 11 by using a hydrophobic polymer in consideration of spin-ability, it is preferable to add a hydrophilic treatment therein, or to use a yarn made of a hydrophilic material such as a cotton yarn or a paper yarn as the covered yarn 21 and/or the intermediate yarn 23 so that more hemostatic agents can be impregnated in the subsequent hemostatic agent impregnating process.

However, it is also possible to use filament yarns made of synthetic fibers such as nylon, polyester-based fibers, polyvinyl chloride-based fibers, polyacrylonitrile-based fibers, and polyimide-based fibers, as the covered yarn 21.

In addition, it is preferable that the nanofiber tape yarn 11 should be plied with the covered yarn 21 in a state in which a tensile force is applied to the nanofiber tape yarn 11 within 10 g to 100 g. If the nanofiber tape yarn is plied and twisted with the covered yarn under the condition that the tensile strength is less than 10 g, the probability that the covered yarn will partially protrude will increase. If the tension exceeds 100 g, yarn breakage may occur during plying.

As a method of imparting tension to the nanofiber tape yarn 11, a tension can be imparted by making a nanofiber tape yarn passing between an up-disk tensor and a down-disk tensor. In addition, the non-tensioned covered yarn 21 and the nanofiber tape yarn 11 having a tensile strength of 10 g to 100 g may be wound on a separate bobbin, during plying, followed by the twisting step with a covering step, and the non-tensioned covered yarn 21 and the tensioned nanofiber tape yarn 11 may be plied together and then continuously subjected to the twisting step by the covering method.

In the twisting step, the covered yarn 21 is uniformly coated with the nanofiber tape yarn 11 and then the nanofiber tape yarn 11 is twisted around the covered yarn 21 by using a twisting machine to produce the nanofiber multiple yarn.

The various kinds of nanofiber multiple yarns 10, 10a and 10b obtained in the above-described producing processes form nanofiber long fibers used as the dental cord of the present invention.

(Heat Treatment and Thermal Stretching Step for Nanofiber Multiple Yarn) (S16)

It is preferable that the nanofiber multiple yarns 10, 10a and 10b obtained by the plying and twisting should be subjected to undergo heat treatment and thermal stretching between the glass transition temperature (Tg) and the melting temperature (Tm) of the polymer used for molecular orientation and strength improvement.

In addition, after the heat treatment of the nanofiber multiple yarn, dyeing of the nanofiber multiple yarn can be performed to improve the size identification and identification in the oral cavity.

This dyeing is done in various colors, the size of the cord can be distinguished by the colors, and the cord can be also easily identified in the oral cavity.

(Hemostatic Agent Impregnation and Drying Step) (S17)

The nanofiber multiple yarn (cord) is immersed in a hemostatic agent, for example, for about 1 hour and then dried.

The powdered hemostatic agent is put in and mixed with, for example, a thickening agent in which water and methyl cellulose are mixed. The hemostatic agent may employ any one of aluminum chloride, aluminum sulfate, and epinephrine, and other known hemostatic agents can be also employed.

(Sterilization Step) (S18)

Figure 8:
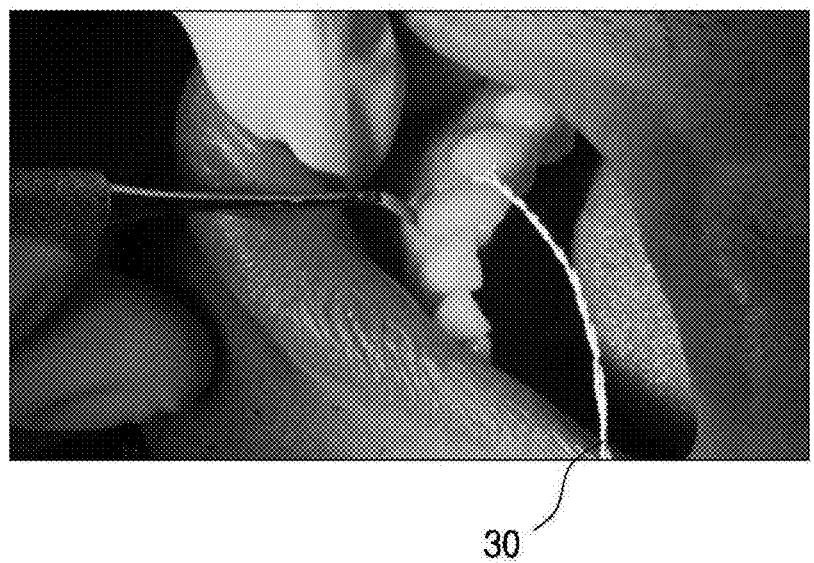
FIG. 8 is a use state photograph showing an operational scene using a dental cord (retraction cord) according to the present invention.

Next, the nanofiber multiple yarn impregnated with the hemostatic agent is irradiated with, for example, gamma-ray and sterilized to obtain a dental cord 30 (see FIG. 8).

Hereinafter, the present invention will be described in more detail with reference to examples. However, the following examples are intended to further illustrate the present invention, and the scope of the present invention is not limited by these examples.

Example

1. Production of PAN Nanofiber Tape Yarn

PAN (polyacrylonitrile) having a molecular weight of 200,000 of Mitsui Chemical Co. Ltd., was dissolved in the solvent DMAc in an amount of 20 wt % to prepare a spinning solution.

This spinning solution was transferred to a spinning nozzle by using a metering pump, and was spun under the conditions of an applied voltage of 25 kV, a distance between a spinneret and a collector of 20 cm, a discharging amount of 0.05 cc/g·hole per minute, a spinning temperature of 30° C., and a relative humidity of 60%, to produce a nanofiber web.

FIG. 3 is a scanning electron microscope (SEM) image of the PAN nanofiber web obtained according to the present embodiment. It can be seen that the nanofiber web is composed of uniform nanofibers having an average diameter of about 500 nm.

The basis weight of the nanofiber web was about 5 gsm. The nanofiber web was laminated at a pressure of 100 g/cm2 by using a roller heated to 100° C. to prepare a PAN polymer membrane having a thickness of about 50 μm. Then, the membrane was slitted to a width of 2 mm using a slitter to produce a PAN nanofiber tape yarn.

2. Production of Multiple Yarn Consisting of PAN Nanofibers

Then, the obtained PAN nanofiber tape yarns were supplied and plied together and wound on the same bobbin. No yarn breakage occurred in the nanofiber tape yarns during plying. A multiple yarn composed of only nanofibers was prepared with a twisted yarn of the nanofiber tape yarn wound on the bobbin by using a twister.

Figure 7:
FIG. 7 is a photograph showing a state where a dental cord (retraction cord) using a nanofiber multiple yarn obtained according to the present invention is wound on a bobbin.

FIGS. 6A and 6B are a scanning electron microscope (SEM) image of a multiple yarn composed of only nanofibers obtained by plying and twisting a nanofiber tape yarn, and FIG. 7 shows nanofiber multiple yarns wound around bobbins.

Meanwhile, the PAN nanofiber tape yarn obtained above and the polyester filament yarn of 75 d (denier) were supplied and plied together and then wound on the same bobbins. Here, the polyester filament yarn was supplied in a non-tensioned state, and the nanofiber tape yarn was supplied with a tensile force of 25 g. No yarn breakage of the nanofiber tape yarn has occurred during plying.

A multiple yarn composed of PAN nanofibers was prepared with a twisted yarn of a polyester filament yarn and a nanofiber tape yarn which were wound around the bobbins, by using a twister. The nanofiber multiple yarn thus obtained had a smooth surface and excellent appearance, and there was observed no portion of the polyester yarn that is a covered yarn, protruding from the surface thereof 3. Manufacture of Dental Cord (Retraction Cord)

Next, the multiple fiber prepared from the PAN nanofibers obtained above was impregnated with a hemostatic agent prepared at a certain concentration and conditions, and then sterilized by gamma-rays to prepare a dental cord (retraction cord). In order to compare the dental cord manufactured by the above method with the commercial product, it was confirmed that no problems were caused in terms of the strength, the hemostatic agent content, and the convenience of the operation procedure, in the result of direct operation as shown in FIG. 8.

FIG. 8 is a use state photograph showing an operational scene using a dental cord (retraction cord) according to the present invention.

As described above, the present invention is not limited to the above embodiment and the accompanying drawings, and it will be apparent to those skilled in the art that various modifications and variations can be made in the present invention without departing from the spirit or scope of the inventions.

INDUSTRIAL APPLICABILITY

The present invention can be applied to the manufacture of a dental cord using a nanofiber multiple yarn having functions of hemostasis and the like.

What is claimed is:

1. A method of manufacturing a dental cord, the method comprising:
    producing a spinning solution by dissolving a fiber-moldable hydrophobic polymer material in a solvent;
    spinning the spinning solution to obtain a polymer nanofiber web composed of nanofibers and including three-dimensional micropores;
    laminating the polymer nanofiber web to obtain a polymer membrane;
    slitting the polymer membrane to obtain a nanofiber tape yarn;
    hydrophilic-treating the nanofiber tape yarn to obtain a hydrophilic-treated nanofiber tape yarn;
    plying and twisting the hydrophilic-treated nanofiber tape yarn with a covered yarn to obtain a nanofiber multiple yarn;
    thermally stretching the nanofiber multiple yarn between a glass transition temperature (Tg) and a melting temperature (Tm) of the fiber-moldable hydrophobic polymer material; and
    impregnating the nanofiber multiple yarn with a hemostatic agent.

2. The method of claim 1, wherein the slitting comprises: slitting the polymer membrane to obtain the nanofiber tape yarn having a width of 0.1 mm to 10 mm.

3. The method of claim 1, wherein the nanofiber tape yarn comprises: at least two nanofiber tape yarns.

4. The method of claim 1, wherein, in the nanofiber multiple yarn, the covered yarn is made of a natural fiber and covered with the hydrophilic-treated nanofiber tape yarn.

5. The method of claim 1, wherein the nanofibers have an average diameter of less than 1 μm.

6. The method of claim 1, wherein the three-dimensional micropores have an average pore size of 0.2 μm to 1.0 μm.

* * * * *